United States Patent
Kim et al.

(10) Patent No.: US 9,244,014 B2
(45) Date of Patent: Jan. 26, 2016

(54) MULTI-CHANNEL FLUORESCENCE DETECTING MODULE AND NUCLEIC ACID ANALYSIS SYSTEM HAVING THE SAME

(71) Applicant: Samsung Electronics Co., Ltd., Suwon-si, Gyeonggi-do (KR)

(72) Inventors: Kyung-ho Kim, Seoul (KR); Won-seok Chung, Suwon-si (KR); Sung-min Chi, Hwaseong-si (KR); Joon-ho Kim, Seongnam-si (KR); Kak Namkoong, Seoul (KR); Chin-sung Park, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/175,554

(22) Filed: Feb. 7, 2014

(65) Prior Publication Data

US 2015/0037876 A1   Feb. 5, 2015

(30) Foreign Application Priority Data

Jul. 31, 2013   (KR) ........................ 10-2013-0091171

(51) Int. Cl.
*G01N 21/64*   (2006.01)

(52) U.S. Cl.
CPC .... *G01N 21/6486* (2013.01); *G01N 2021/6421* (2013.01); *G01N 2201/062* (2013.01); *G01N 2201/0612* (2013.01); *G01N 2201/103* (2013.01); *G01N 2201/1053* (2013.01)

(58) Field of Classification Search
CPC ............ G01N 2035/00524; G01N 2035/0413; G01N 2035/0415; G01N 2035/0475; G01N 2035/1048; G01N 2035/1051; G01N 2035/1076; G01N 2021/6421; G01N 21/6486; G01N 2201/0612; G01N 2201/062; G01N 2201/103
USPC ....................................... 250/461.1
See application file for complete search history.

(56) References Cited

U.S. PATENT DOCUMENTS

| | | | |
|---|---|---|---|
| 4,974,104 A | 11/1990 | Ferguson et al. | |
| 6,323,935 B1 | 11/2001 | Ebihara et al. | |
| 6,617,590 B2 * | 9/2003 | Nishioka et al. | 250/459.1 |
| 6,902,112 B2 * | 6/2005 | Sadler et al. | 235/454 |
| 7,125,660 B2 * | 10/2006 | Stanton et al. | 435/4 |
| 7,947,442 B2 * | 5/2011 | Iten | 435/6.12 |

(Continued)

FOREIGN PATENT DOCUMENTS

| KR | 100715157 B1 | 10/2007 |
|---|---|---|
| KR | 1020120116778 A | 10/2012 |

*Primary Examiner* — Mark R Gaworecki
*Assistant Examiner* — Taeho Jo
(74) *Attorney, Agent, or Firm* — Leydig, Voit & Mayer, Ltd.

(57) ABSTRACT

Provided are a multi-channel fluorescence detecting module and a nucleic acid analysis system including the multi-channel fluorescence detecting module. The nucleic acid analysis system includes: a plurality of loaders configured to accommodate a plurality of cartridges respectively, the cartridges comprising microfluidic devices; a transfer module including a linear actuator, the linear actuator including a movable unit configured to move linearly; and a fluorescence detecting module fixed to the movable unit, the fluorescence detecting module being configured to emit excitation light to the cartridges and detect fluorescence emitted from samples on the cartridges. The loaders are arranged in a row in a linearly moving direction of the movable unit.

14 Claims, 7 Drawing Sheets

(56) References Cited

U.S. PATENT DOCUMENTS

| | | | |
|---|---|---|---|
| 2004/0061049 A1* | 4/2004 | Curry et al. | 250/282 |
| 2006/0246493 A1* | 11/2006 | Jensen et al. | 435/6 |
| 2010/0126857 A1* | 5/2010 | Polwart et al. | 204/403.14 |
| 2012/0033210 A1 | 2/2012 | Kolesnychenko et al. | |
| 2012/0146432 A1* | 6/2012 | Kim et al. | 310/12.16 |
| 2012/0305801 A1* | 12/2012 | Kim et al. | 250/458.1 |
| 2012/0318956 A1* | 12/2012 | Yamaguchi et al. | 250/203.3 |
| 2013/0070148 A1 | 3/2013 | Kim | |
| 2013/0122488 A1* | 5/2013 | Tanabe et al. | 435/5 |
| 2013/0210127 A1* | 8/2013 | Williams et al. | 435/287.2 |
| 2013/0302906 A1* | 11/2013 | Tanabe | 436/172 |

\* cited by examiner

MULTI-CHANNEL FLUORESCENCE DETECTING MODULE AND NUCLEIC ACID ANALYSIS SYSTEM HAVING THE SAME

CROSS-REFERENCE TO RELATED APPLICATIONS

This application claims the benefit of Korean Patent Application No. 10-2013-0091171, filed on Jul. 31, 2013, in the Korean Intellectual Property Office, the entire disclosure of which is hereby incorporated by reference.

BACKGROUND

1. Field

The present disclosure relates to multi-channel fluorescence detecting modules and nucleic acid analysis systems including the multi-channel fluorescence detecting modules, and more particularly, to multi-channel fluorescence detecting modules and nucleic acid analysis systems capable of analyzing nucleic acid samples disposed on microfluidic device cartridges in real time by using the multi-channel fluorescence detecting modules including a linear actuator.

2. Description of the Related Art

With the advance of point-of-care technology, there is increasing interest in gene analysis, in vitro diagnosis, and gene sequence analysis, and demand therefor is also increasing. Platforms and systems for rapidly performing a large amount of analysis using small amounts of samples have been developed and introduced into the market. For example, there is interest in microfluidic devices or platforms such as lab-on-a-chip devices. Such a microfluidic device includes a plurality of microfluidic channels and chambers to control and process a small amount of a fluid. The use of microfluidic devices reduces time periods of microfluidic reactions and allows microfluidic reactions and measurements of the microfluidic reactions to take place at the same time. Such microfluidic devices are manufactured by various methods, and various materials are used according to the manufacturing methods.

For example, in a gene analysis, a sample may be refined/extracted and amplified to obtain a sufficient amount of sample for analyzing whether the sample has a certain kind of DNA or precisely detecting the amount of a certain kind of DNA. For example, polymerase chain reaction (PCR) is most widely used among the various gene amplifying methods. A fluorescence detection method is widely used for detecting DNA amplified by PCR. In quantitative real-time PCR (qPCR), a plurality of fluorescent dyes/probes and a set of primers are used to amplify a target sample and detect/measure the amplified target sample in real time.

In qPCR using TaqMan probes, TaqMan probes separated from templates in a DNA amplifying stage become fluorescent. That is, as qPCR proceeds, the number of TaqMan probes separated from templates is exponentially increased, and thus the level of a fluorescence signal is also exponentially increased. Therefore, a target sample may be detected or quantitatively analyzed by measuring variations of the level of such a fluorescence signal. As the number of PCR cycles increases, the shape of a fluorescence signal curve follows an S-curve, and a point at which the shape of the fluorescence signal curve is largely varied is measured and determined as a threshold cycle (Ct). qPCR platforms for in vitro diagnosis, gene analysis, bio marking, and gene sequence analysis have been commercialized.

In the case of nucleic acid analysis systems of the related art using step motors, a transfer module may scan only a single cartridge because the positional precision and driving speed of the step motors are limited. Therefore, in order to analyze nucleic acids for a plurality of cartridges, a plurality of transfer modules on which fluorescence detecting modules are respectively disposed are used. That is, nucleic acid analysis systems of the related art include as many transfer modules and fluorescence detecting modules as the number of cartridges to be analyzed at a time. In the related art, as a result, it is difficult to reduce the size of nucleic acid analysis system. In addition, since a plurality of fluorescence detecting modules including expensive optical components are used, it is difficult to reduce the manufacturing costs of nucleic acid analysis systems of the related art. Furthermore, the use of a plurality of step motors results in a large amount of noise.

SUMMARY

Additional aspects will be set forth in part in the description which follows and, in part, will be apparent from the description, or may be learned by practice of the presented embodiments.

According to an aspect of an exemplary embodiment of the present invention, a nucleic acid analysis system includes: a plurality of loaders configured to accommodate a plurality of cartridges respectively, the cartridges including microfluidic devices; a transfer module including a linear actuator, the linear actuator including a movable unit configured to move linearly; and a fluorescence detecting module fixed to the movable unit, the fluorescence detecting module configured to emit excitation light to the cartridges and detect fluorescence emitted from samples in the cartridges, wherein the loaders are arranged in a row in a linearly moving direction of the movable unit.

The linear actuator may include a VCM (voice coil motor). The VCM may include: the movable unit, including a coil and a bobbin around which the coil is wound; and a stator including magnets and a yoke to which the magnets are fixed. The linear actuator may further include: a printed circuit board including a control circuit to control movement of the movable unit and an encoder to detect a position of the movable unit; and a shaft configured to support the movable unit and guide movement of the movable unit. The encoder may include a magnetic or optical encoder. The encoder may be disposed on a bottom side of the printed circuit board to face the movable unit.

Each of the loaders may include: a heating unit configured to control temperature of the cartridge on the loader; and a cartridge detecting sensor configured to detect whether a cartridge is on the loader.

The fluorescence detecting module may include at least two two-color fluorescence detecting optical systems each capable of detecting two wavelengths of fluorescence. The fluorescence detecting module may include: a first fluorescence detecting optical system configured to detect fluorescence using a first excitation light and a second excitation light of different wavelengths; and a second fluorescence detecting optical system configured to detect fluorescence using a third excitation light and a fourth excitation light of different wavelengths.

The first fluorescence detecting optical system may include: a first objective lens configured to focus light on a reaction chamber of one of the plurality of cartridges; first and second light sources configured to emit the first excitation light and the second excitation light, respectively; a first dichroic mirror configured to reflect the first excitation light; a second dichroic mirror configured to reflect the second excitation light; a third dichroic mirror configured to reflect the first excitation light to the first objective lens and transmit the second excitation light to the first objective lens; a first photodetector configured to detect a first fluorescence emitted from a sample in the cartridge in response to the first excitation light; and a second photodetector configured to detect a second fluorescence emitted from the sample in the cartridge in response to the second excitation light.

The first fluorescence detecting optical system may further include: a first collimating lens disposed proximal to the first light source to collimate the first excitation light; a first excitation light filter configured to transmit only wavelengths of the first excitation light; a second collimating lens disposed proximal to the second light source to collimate the second excitation light; and a second excitation light filter configured to transmit only wavelengths of the second excitation light.

The first fluorescence detecting optical system may further include: a first fluorescence filter configured to transmit only the first fluorescence; a first focusing lens disposed between the first fluorescence filter and the first photodetector to focus the first fluorescence on the first photodetector; a second fluorescence filter configured to transmit only the second fluorescence; and a second focusing lens disposed between the second fluorescence filter and the second photodetector to focus the second fluorescence on the second photodetector.

The first light source may emit a blue excitation light, and the second light source may emit an amber excitation light.

The first dichroic mirror may be configured to reflect a wavelength band of the first excitation light and transmit a wavelength band of the first fluorescence, the second dichroic mirror may be configured to reflect a wavelength band of the second excitation light and transmit a wavelength band of the second fluorescence, and the third dichroic mirror may be configured to reflect wavelength bands of the first excitation light and the first fluorescence and transmit wavelength bands of the second excitation light and the second fluorescence.

The first light source and the second photodetector may be disposed adjacent to each other on a first plane, and the second light source and the first photodetector may be disposed adjacent to each other on a second plane perpendicular to the first plane.

The second fluorescence detecting optical system may include: a second objective lens configured to focus light on a reaction chamber of one of the plurality of cartridges; third and fourth light sources configured to emit the third excitation light and fourth excitation light, respectively; a fourth dichroic mirror configured to reflect the third excitation light; a fifth dichroic mirror configured to reflect the fourth excitation light; a sixth dichroic mirror configured to reflect the third excitation light to the second objective lens and transmit the fourth excitation light to the second objective lens; a third photodetector configured to detect a third fluorescence emitted from a sample in the cartridge in response to the third excitation light; and a fourth photodetector configured to detect a fourth fluorescence emitted from the sample in the cartridge in response to the fourth excitation light.

The third light source may emit a green excitation light, and the fourth light source may emit a red light source.

The fourth dichroic mirror may be configured to reflect a wavelength band of the third excitation light and transmit a wavelength band of the third fluorescence, the fifth dichroic mirror may be configured to reflect a wavelength band of the fourth excitation light and transmit a wavelength band of the fourth fluorescence, and the sixth dichroic mirror may be configured to reflect wavelength bands of the third excitation light and the third fluorescence and transmit wavelength bands of the fourth excitation light and the fourth fluorescence.

The third light source and the fourth photodetector may be disposed adjacent to each other on a third plane, and the fourth light source and the third photodetector may be disposed adjacent to each other on a fourth plane perpendicular to the third plane.

BRIEF DESCRIPTION OF THE DRAWINGS

These and/or other aspects will become apparent and more readily appreciated from the following description of the embodiments, taken in conjunction with the accompanying drawings, in which.

DETAILED DESCRIPTION

Reference will now be made in detail to embodiments, examples of which are illustrated in the accompanying drawings. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a multi-channel fluorescence detecting module and a nucleic acid analysis system including the multi-channel fluorescence detecting module will be described with reference to the accompanying drawings. The size of each element may be exaggerated for clarity of illustration.

Figure 1:
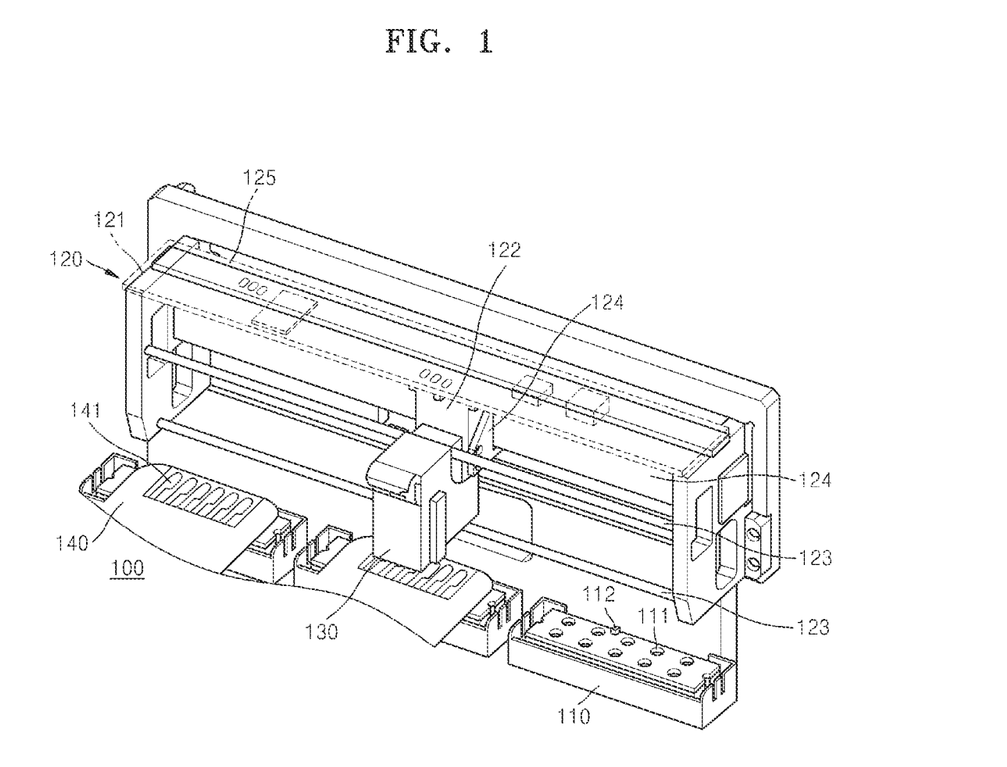
FIG. 1 is a schematic perspective view of a nucleic acid analysis system.

FIG. 1 is a schematic perspective view illustrating a nucleic acid analysis system 100 according to an embodiment. Referring to FIG. 1, in the nucleic acid analysis system 100, a series of processes may be automatically performed using microfluidic device cartridges 140 (hereinafter simply referred to as cartridges 140) including microfluidic devices so as to process various samples for extracting and amplifying nucleic acids and analyzing the nucleic acids. For this end, the nucleic acid analysis system 100 may include: a plurality of loaders 110 for placing cartridges 140 thereon respectively; a fluorescence detecting module 130 configured to analyze fluorescence emitted from samples in the cartridges 140; and a transfer module 120 configured to move the fluorescence detecting module 130 for scanning the cartridges 140. The cartridges 140 may be detachably attached to the nucleic acid analysis system 100 so that an analyzed cartridge 140 may be replaced with another cartridge 140 not yet analyzed.

Each of the cartridges 140 may include a plurality of reaction chambers 141 in which samples undergo reactions such as a polymerase chain reaction (PCR). The fluorescence detecting module 130 may sequentially emit excitation light to the reaction chambers 141 and detect the intensity of fluorescence emitted from samples in the reaction chambers 141 in response to the excitation light. The transfer module 120 may sequentially move the fluorescence detecting module 130 to the reaction chambers 141 of the cartridges 140. After fluorescence emitted from a sample of a cartridge 140 is analyzed, the transfer module 120 may move the fluorescence detecting module 130 to the next cartridge 140.

The transfer module 120 may include a linear actuator having a linearly movable unit. For example, the linear actuator may be a voice coil motor (VCM). The VCM may include: a movable unit 122 having a coil and a bobbin around which the coil is wound; a stator 124 having magnets and a yoke to which the magnets are fixed. If a current is applied to the coil of the movable unit 122, the magnets and the coil interact with each other according to Fleming's left-hand rule so that the movable unit 122 may move to the left or right. The transfer module 120 may include: a printed circuit board 121 having a control circuit to control movement of the movable unit 122 and an encoder 125 to detect the absolute position of the movable unit 122; and a shaft 123 configured to support the movable unit 122 and guide movement of the movable unit 122. The fluorescence detecting module 130 may be fixed to the movable unit 122 for moving together with the movable unit 122.

The encoder 125 is used to precisely detect the position of the movable unit 122. Fine coordinate codes are formed on the encoder 125. The position of the movable unit 122 may be precisely detected by reading the coordinate codes of the encoder 125. Precision in controlling the position of the movable unit 122 may be determined according to the precision of the encoder 125. For example, the precision of the encoder 125 may be selected from the range of several tens of nanometers (nm) to several micrometers (µm). The encoder 125 may a magnetic or optical encoder. The encoder 125 may be disposed on the bottom side of the printed circuit board 121 to face the movable unit 122, and a sensor may be attached to the movable unit 122 to read the encoder 125. For example, if the encoder 125 is a magnetic encoder, a Hall sensor may be attached to the movable unit 122.

In an embodiment, a linear actuator such as a VCM operating with low-noise, high-speed, and high-positional-accuracy conditions is used as the transfer module 120 so that the plurality of cartridges 140 may be rapidly scanned and randomly accessed using only the single transfer module 120. Therefore, as shown in FIG. 1, in the nucleic acid analysis system 100, a plurality of loaders 110 on which a plurality of cartridges 140 will be respectively disposed may be arranged with respect to the single transfer module 120. The loaders 110 may be arranged in a linearly moving direction of the movable unit 122. Although three loaders 110 are illustrated in FIG. 1, the number of the loaders 110 is not limited as such.

As shown in FIG. 1, each of the loaders 110 may include: a heating unit 111 to control the temperature of a cartridge 140, and a cartridge detecting sensor 112 to detect whether a cartridge 140 is on the loader 110. The cartridge detecting sensor 112 may be an optical sensor or a micro switch.

The nucleic acid analysis system 100 may operate as follows. First, when cartridges 140 are disposed on the loaders 110, the cartridge detecting sensors 112 detect the cartridges 140. Cartridges 140 may be detected on one or more of the plurality of loaders 110. The transfer module 120 then moves the fluorescence detecting module 130 to an initial position. The initial position may be the center, a left edge position, or a right edge position of a total scan width in a linearly moving direction of the transfer module 120. The initial position also may be located between cartridges 140. Thereafter, the transfer module 120 is operated to scan the cartridges 140. For example, the transfer module 120 may move the fluorescence detecting module 130 above the reaction chambers 141 of the cartridges 140 in a preset order. The positions of the reaction chambers 141 of the cartridges 140 in the loaders 110 may be input before the operation of the nucleic acid analysis system 100. In this case, the transfer module 120 may move the fluorescence detecting module 130 to a target reaction chamber 141 while detecting the position of the fluorescence detecting module 130 by reading the encoder 125.

Figure 2:
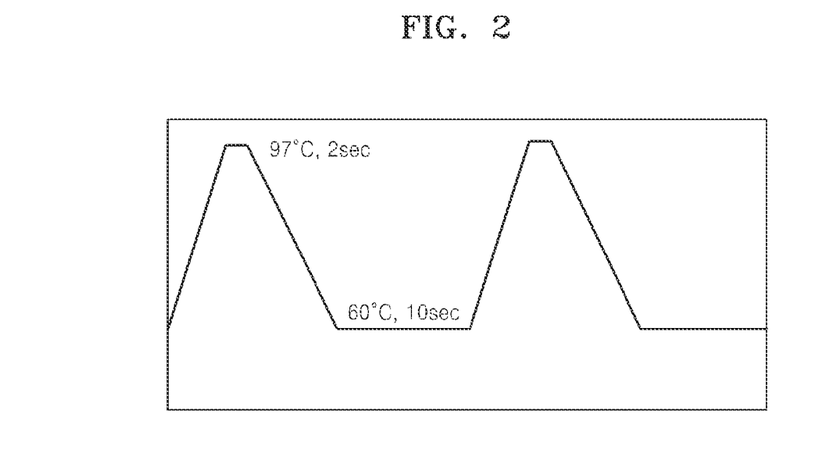
FIG. 2 is a temperature profile graph for a polymerase chain reaction (PCR)

FIG. 2 is an illustrative temperature profile graph for PCR. Referring to FIG. 2, a rapid PCR process may be performed by maintaining the reaction chambers 141 at 97° C. for two (2) seconds for thermal denaturation and at 60° C. for ten (10) seconds for extension by DNA polymerase. Fluorescence may be detected using the fluorescence detecting module 130 at about a 8.5-second point in the time period of extension.

Figure 3:
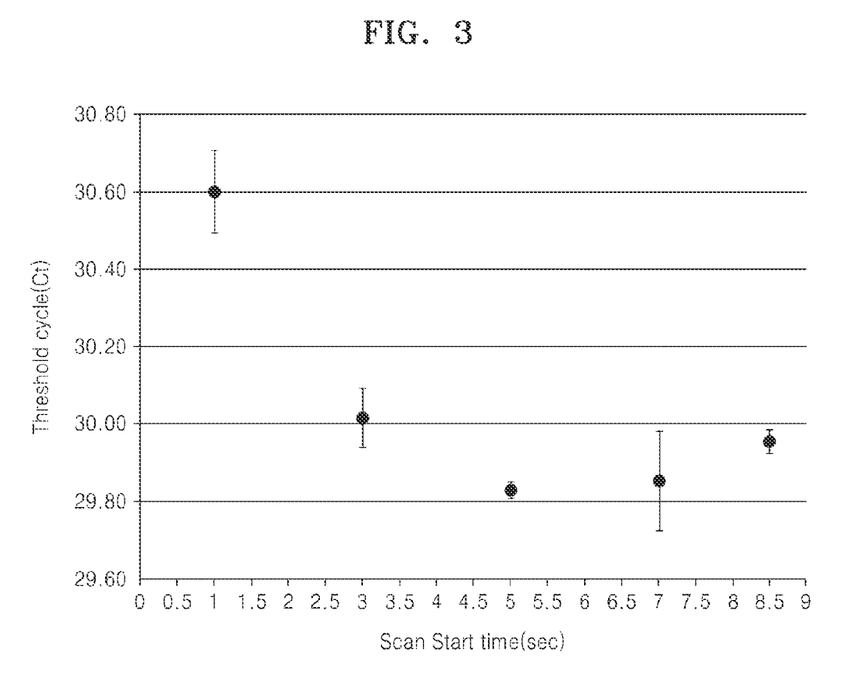
FIG. 3 is a graph illustrating the relationship between the threshold cycle (Ct) of PCR and the start time of scanning for detecting fluorescence.

However, since fluorescence emitted from the plurality of reaction chambers 141 is measured, the threshold cycle (Ct) of PCR may be affected if measuring times of the fluorescence are different. FIG. 3 is a graph illustrating the relationship between a scan start time and the threshold cycle (Ct) of PCR for SA442 gDNA having a low concentration of about $10^2$ copies/µl. Referring to FIG. 3, the threshold cycle (Ct) of PCR is largely varied in an early stage of the time period of extension but is less varied at about an 8.5-second point in the time period of extension. Therefore, if all the reaction chambers 141 are scanned within the range of about 8.0 seconds to about 9.0 seconds in the time period of extension, the threshold cycle (Ct) of PCR may not vary substantially. Since the transfer module 120 of the nucleic acid analysis system 100 has a high operating speed, a real-time fluorescence analysis may be precisely performed on reaction chambers 141 of cartridges 140 without substantial variance of the threshold cycle (Ct) of PCR.

As described above, the nucleic acid analysis system 100 uses a linear actuator such as a VCM, and nucleic acids contained in the plurality of cartridges 140 may be analyzed using the single transfer module 120 and the single fluorescence detecting module 130, improving the efficiency of analysis, and permitting various samples to be analyzed at the same time to reduce the time period of analysis. In addition, since only the single transfer module 120 and the single fluorescence detecting module 130 are used, the nucleic acid analysis system 100 may be small and inexpensive. Furthermore, the nucleic acid analysis system 100 may have high-speed, low-noise characteristics owing to the linear actuator.

Figure 4:
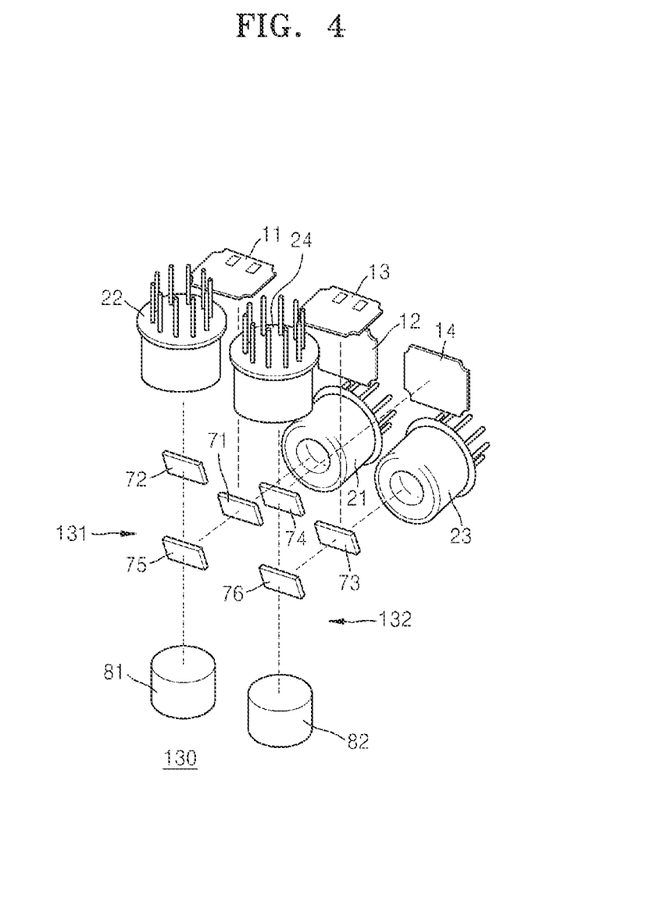
FIG. 4 is a schematic perspective view of a multi-channel fluorescence detecting module including multi-channel fluorescence detecting optical systems.

The fluorescence detecting module 130 may be configured to detect fluorescence of different wavelength bands at the same time so as to detect various gDNAs. FIG. 4 is a schematic perspective view illustrating the fluorescence detecting module 130, which includes multi-channel fluorescence detecting optical systems. Referring to FIG. 4, the fluorescence detecting module 130 may include two two-color fluorescence detecting optical systems 131 and 132 each capable of detecting two wavelengths of fluorescence. That is, the fluorescence detecting module 130 may detect four wavelengths of fluorescence. Although two (first and second) fluorescence detecting optical systems 131 and 132 are shown in FIG. 4, the fluorescence detecting module 130 may include additional fluorescence detecting optical systems. In the case where the fluorescence detecting module 130 includes two fluorescence detecting optical systems 131 and 132, the fluorescence detecting module 130 may include four (first to fourth) light sources 11, 12, 13, and 14, and four (first to fourth) photodetectors 21, 22, 23, and 24.

Figure 5:
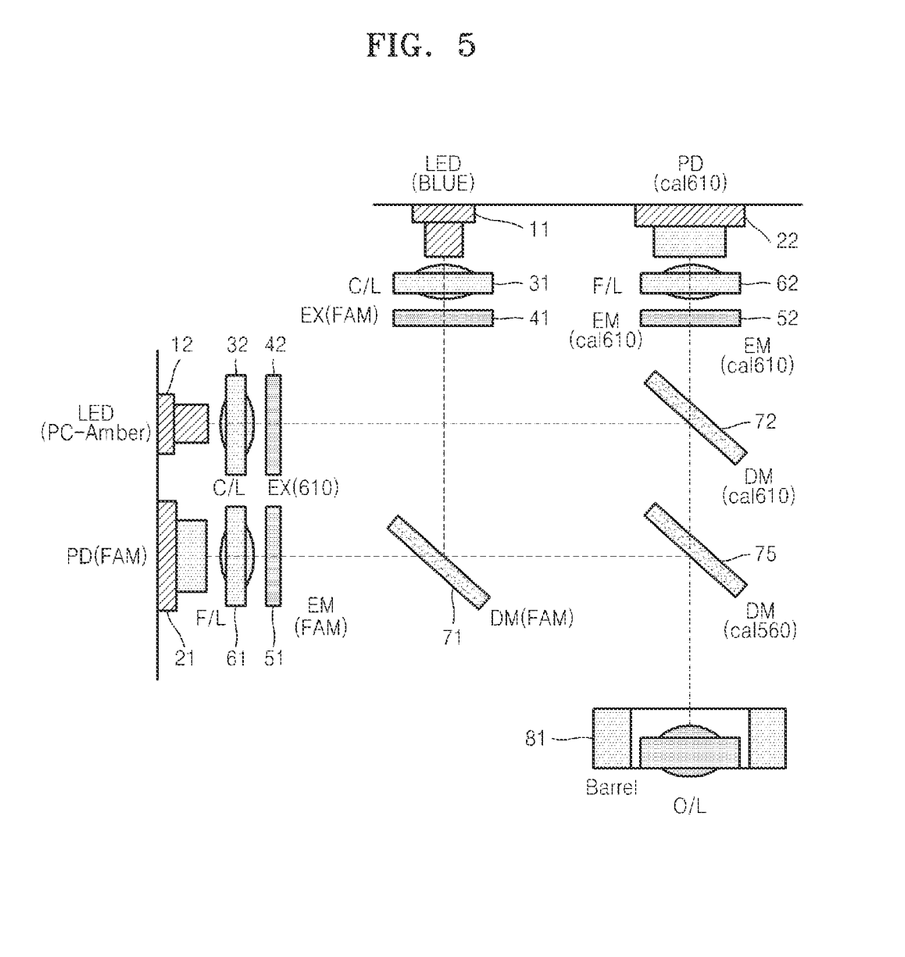
FIG. 5 is a schematic view of a first fluorescence detecting optical system illustrated in FIG. 4.

FIG. 5 is a schematic view illustrating the first fluorescence detecting optical system 131 illustrated in FIG. 4. Referring to FIG. 5, the first fluorescence detecting optical system 131 may include a first objective lens 81 configured to focus light on a reaction chamber 141 of a cartridge 140, the first and second light sources 11 and 12 emitting excitation light of different wavelengths, a first dichroic mirror 71 configured to reflect the first excitation light emitted from the first light source 11, a second dichroic mirror 72 configured to reflect the second excitation light emitted from the second light source 12, a third dichroic mirror 75 configured to reflect the first excitation light to the first objective lens 81 and transmit the second excitation light to the first objective lens 81, the first photodetector 21 configured to detect a first fluorescence emitted from a sample in the cartridge 140 in response to the first excitation light, and the second photodetector 22 configured to detect a second fluorescence emitted from the sample in the cartridge 140 in response to the second excitation light.

In addition, the first fluorescence detecting optical system 131 may further include a first collimating lens 31 configured to collimate the first excitation light, a first excitation light filter 41 configured to transmit only wavelengths of the first excitation light, a second collimating lens 32 configured to collimate the second excitation light, a second excitation light filter 42 configured to transmit only wavelengths of the second excitation light, a first fluorescence filter 51 configured to transmit only the first fluorescence, a first focusing lens 61 disposed between the first fluorescence filter 51 and the first photodetector 21 to focus the first fluorescence on the first photodetector 21, a second fluorescence filter 52 configured to transmit only the second fluorescence, and a second focusing lens 62 disposed between the second fluorescence filter 52 and the second photodetector 22 to focus the second fluorescence on the second photodetector 22.

Figure 6:
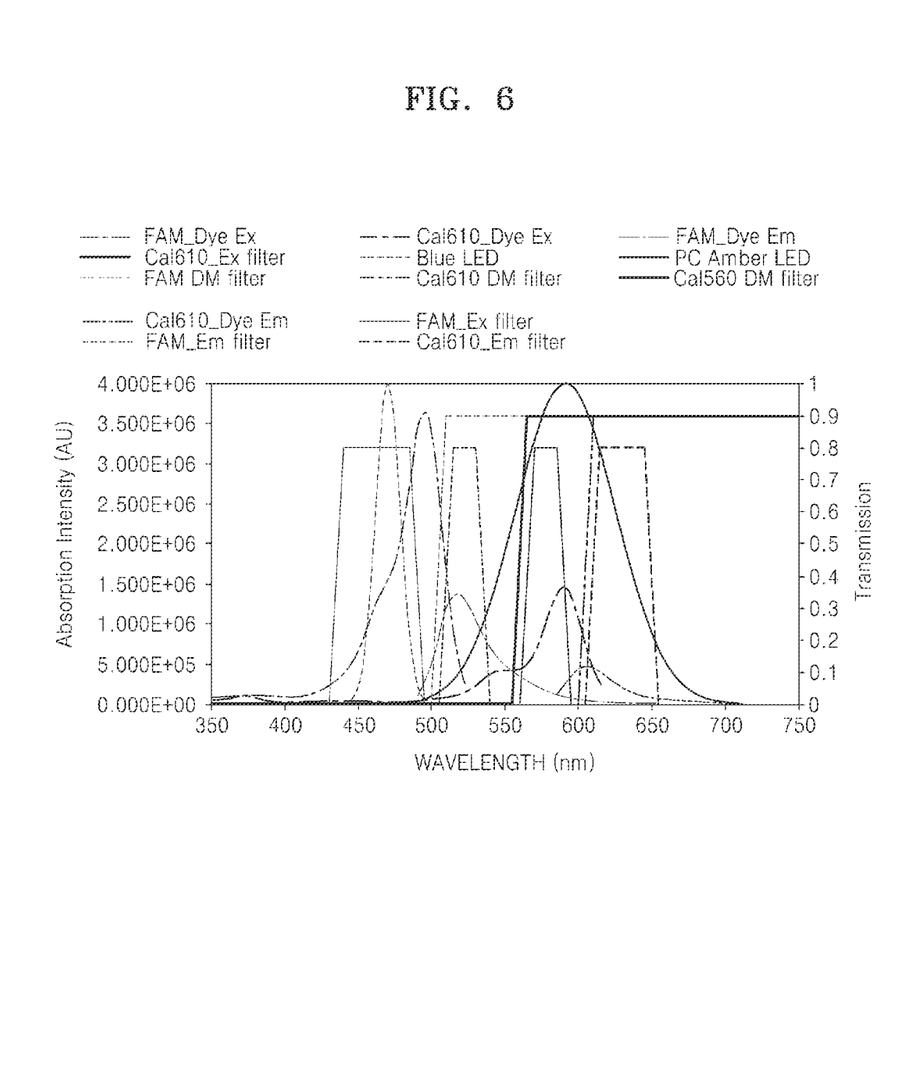
FIG. 6 is a graph illustrating wavelength bands of a plurality of light sources, a plurality of excitation light filters, and a plurality of fluorescence filters of the first fluorescence detecting optical system illustrated in FIG. 5, and wavelength bands of fluorescence emitted from a sample.

The first and second light sources 11 and 12 may be light emitting diodes (LEDs), laser diodes (LDs), or halogen lamps emitting excitation light of different wavelengths. For example, the wavelengths of excitation light emitted from the first and second light sources 11 and 12 may be selected from blue, green, amber, and red wavelengths. To minimize crosstalk, the first and second light sources 11 and 12 may have different wavelength bands that do not overlap each other. For example, if the first light source 11 is an LED emitting blue excitation light, the second light source 12 may be an LED emitting amber excitation light. In another example, if the first light source 11 is an LED emitting green excitation light, the second light source 12 may be an LED emitting red excitation light. In the example shown in FIG. 5, the first light source 11 emits blue excitation light, and the second light source 12 emits amber excitation light. FIG. 6 shows illustrative wavelength bands of the first and second light sources 11 and 12, the first and second excitation light filters 41 and 42, the first and second fluorescence filters 51 and 52, the first to third dichroic mirrors 71, 72, and 75 of the first fluorescence detecting optical system 131, and wavelength bands of the fluorescence emitted from a sample for the case where the first light source 11 emits blue excitation light and the second light source 12 emits amber excitation light.

The first and second excitation light filters 41 and 42 are disposed proximal to the first and second light sources 11 and 12, respectively, to transmit only desired components of excitation light. The first excitation light filter 41 may be a band pass filter configured to transmit only a wavelength band of the first excitation light, and the second excitation light filter 42 may be a band pass filter configured to transmit only a wavelength band of the second excitation light. For example, the first excitation light filter 41 may be a band pass filter configured to transmit only a blue wavelength band, and the second excitation light filter 42 may be a band pass filter configured to transmit only an amber wavelength band.

The first photodetector 21 is used to detect a first fluorescence emitted from a sample excited by the first excitation light, and the second photodetector 22 is used to detect a second fluorescence emitted from the sample excited by the second excitation light. For this, the first fluorescence filter 51 being a band pass filter capable of transmitting only the first fluorescence and blocking other light may be disposed proximal to the first photodetector 21. In addition, the second fluorescence filter 52 being a band pass filter capable of transmitting only the second fluorescence and blocking other light may be disposed proximal to the second photodetector 22. The first and second photodetectors 21 and 22 may include photodiodes, photodiode arrays, photo multiplier tubes (PMTS), charge-coupled device (CCD) image sensors, complementary metal-oxide semiconductor (CMOS) image sensors, or avalanche photodiodes (APDs).

In the above-described configuration, the first excitation light emitted from the first light source 11 is reflected by the first dichroic mirror 71. As shown in FIG. 6, the center wavelength of the first excitation light may be about 460 nm after the first excitation light passes through the first excitation light filter 41, and the first dichroic mirror 71 may reflect wavelengths of the first excitation light shorter than about 500 nm and may transmit wavelengths of the first excitation light longer than about 500 nm. The first excitation light reflected by the first dichroic mirror 71 is reflected by the third dichroic mirror 75. As shown in FIG. 6, the third dichroic mirror 75 may reflect wavelengths shorter than about 550 nm and may transmit wavelengths longer than about 550 nm. Thereafter, the first excitation light may be focused on a sample by the first objective lens 81 so as to excite the sample. The first fluorescence emitted from the sample excited by the first excitation light may have a wavelength of about 520 nm as shown in FIG. 6. Therefore, the first fluorescence may be reflected by the third dichroic mirror 75. Then, the first fluorescence may pass through the first dichroic mirror 71 and reach the first photodetector 21.

Second excitation light emitted from the second light source 12 is reflected by the second dichroic mirror 72. As shown in FIG. 6, the center wavelength of the second excitation light may be about 580 nm after the second excitation light passes through the second excitation light filter 42, and the second dichroic mirror 72 may reflect wavelengths of the second excitation light shorter than about 600 nm and may transmit wavelengths of the second excitation light longer than about 600 nm. The second excitation light reflected by the second dichroic mirror 72 passes through the third dichroic mirror 75. As shown in FIG. 6, the third dichroic mirror 75 may reflect wavelengths shorter than about 550 nm and may transmit wavelengths longer than about 550 nm. Thereafter, the second excitation light may be focused on the sample by the first objective lens 81 so as to excite the sample. The second fluorescence emitted from the sample excited by the second excitation light may have a wavelength of about 620 nm as shown in FIG. 6. Therefore, the second fluorescence may pass through the third dichroic mirror 75 and the second dichroic mirror 72 and reach the second photodetector 22.

As described above, the first fluorescence detecting optical system 131 may perform two-color fluorescence detecting procedures while minimizing crosstalk. In addition, referring to FIG. 5, the first light source 11 and the second photodetector 22 are disposed adjacent to each other on a first plane, and the second light source 12 and the first photodetector 21 are disposed adjacent to each other on a second plane substantially perpendicular to the first plane. Therefore, by using only the three dichroic mirrors 71, 72, and 75, two excitation light beams may be focused on the same sample, and two fluorescence beams emitted from the sample may be directed to the first and second photodetectors 21 and 22, respectively. Therefore, the first fluorescence detecting optical system 131 may have a compact shape.

Figure 7:
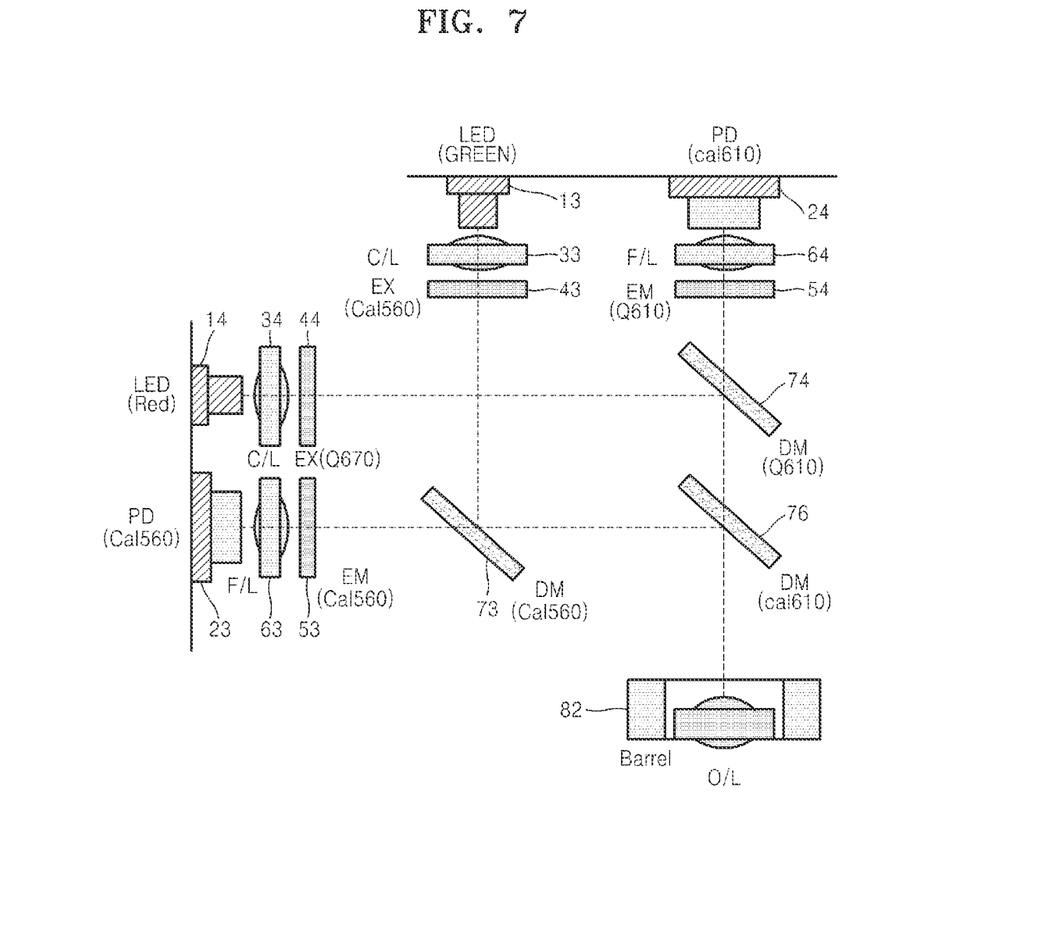
FIG. 7 is a schematic view of a second fluorescence detecting optical system illustrated in FIG. 4.

FIG. 7 is a schematic view illustrating the second fluorescence detecting optical system 132 illustrated in FIG. 4. Referring to FIG. 7, the second fluorescence detecting optical system 132 may include a second objective lens 82 configured to focus light on a reaction chamber 141 of a cartridge 140, the third and fourth light sources 13 and 14 emitting excitation light of different wavelengths, a fourth dichroic mirror 73 configured to reflect the third excitation light emitted from the third light source 13, a fifth dichroic mirror 74 configured to reflect the forth excitation light emitted from the fourth light source 14, a sixth dichroic mirror 76 configured to reflect the third excitation light to the second objective lens 82 and transmit fourth excitation light to the second objective lens 82, the third photodetector 23 configured to detect the third fluorescence emitted from a sample in the cartridge 140 in response to the third excitation light, and the fourth photodetector 24 configured to detect the fourth fluorescence emitted from a sample in the cartridge 140 in response to the fourth excitation light.

In addition, the second fluorescence detecting optical system 132 may further include a third collimating lens 33 configured to collimate the third excitation light, a third excitation light filter 43 configured to transmit only wavelengths of the third excitation light, a fourth collimating lens 34 configured to collimate the fourth excitation light, a fourth excitation light filter 44 configured to transmit only wavelengths of the fourth excitation light, a third fluorescence filter 53 configured to transmit only the third fluorescence, a third focusing lens 63 disposed between the third fluorescence filter 53 and the third photodetector 23 to focus third fluorescence on the third photodetector 23, a fourth fluorescence filter 54 configured to transmit only the fourth fluorescence, and a fourth focusing lens 64 disposed between the fourth fluorescence filter 54 and the fourth photodetector 24 to focus the fourth fluorescence on the fourth photodetector 24.

Figure 8:
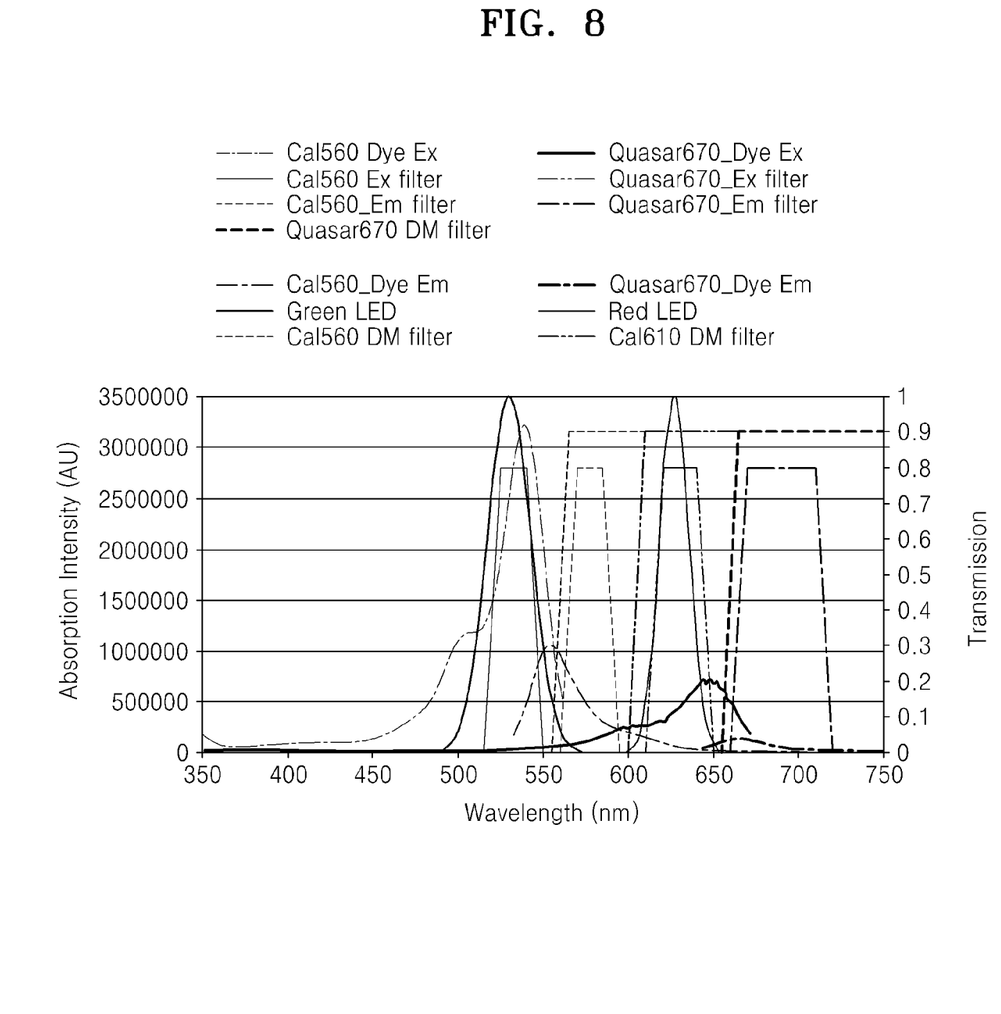
FIG. 8 is a graph illustrating wavelength bands of a plurality of light sources, a plurality of excitation light filters, and a plurality of fluorescence filters of the second fluorescence detecting optical system illustrated in FIG. 7, and wavelength bands of fluorescence emitted from a sample.

As described above, the wavelengths of excitation light emitted from the third and fourth light sources 13 and 14 may be selected from blue, green, amber, and red, so as to minimize crosstalk. In the example shown in FIG. 7, the third light source 13 emits green excitation light, and the fourth light source 14 emits red excitation light. FIG. 8 illustrates exemplary wavelength bands of the third and fourth light sources 13 and 14, the third and fourth excitation light filters 43 and 44, the third and fourth fluorescence filters 53 and 54, the fourth to sixth dichroic mirrors 73, 74, and 76 of the second fluorescence detecting optical system 132, and wavelength bands of fluorescence emitted from a sample for the case where the third light source 13 emits green excitation light and the fourth light source 14 emits red excitation light.

The above descriptions of the configuration and operation of the first fluorescence detecting optical system 131 may be applied to the second fluorescence detecting optical system 132 except for wavelength bands of excitation light and fluorescence. Thus, descriptions of the configuration and operation of the second fluorescence detecting optical system 132 will be omitted. Referring to FIG. 7, in the second fluorescence detecting optical system 132, the third light source 13 and the fourth photodetector 24 are disposed adjacent to each other on a third plane, and the fourth light source 14 and the third photodetector 23 are disposed adjacent to each other on a fourth plane substantially perpendicular to the third plane. Therefore, by using only the three dichroic mirrors 73, 74, and 76, two excitation light beams may be focused on the same sample, and two fluorescence beams emitted from the sample may be directed to the third and fourth photodetectors 23 and 24, respectively. Therefore, the second fluorescence detecting optical system 132 may have a compact shape. As described above, the first and second fluorescence detecting optical systems 131 and 132 may have fewer optical components and compact shapes, and thus the fluorescence detecting module 130 may be small and light.

The multi-channel fluorescence detecting module and the nucleic acid analysis system including the multi-channel fluorescence detecting module are described according to the various embodiments with reference to the accompanying drawings. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nucleic acid analysis system comprising:
   a plurality of loaders configured to accommodate a plurality of cartridges respectively, the cartridges comprising microfluidic devices;
   a transfer module comprising a linear actuator, the linear actuator comprising a movable unit configured to move linearly; and
   a fluorescence detecting module fixed to the movable unit, the fluorescence detecting module configured to emit excitation light to the cartridges and detect fluorescence emitted from samples on the cartridges,
   wherein the loaders are arranged in a row in a linearly moving direction of the movable unit.

2. The nucleic acid analysis system of claim 1, wherein the linear actuator comprises a VCM (voice coil motor), and the VCM comprises:
   the movable unit, comprising a coil and a bobbin around which the coil is wound; and
   a stator comprising magnets and a yoke to which the magnets are fixed.

3. The nucleic acid analysis system of claim 2, wherein the linear actuator further comprises:
   a printed circuit board comprising a control circuit to control movement of the movable unit and an encoder to detect a position of the movable unit; and
   a shaft configured to support the movable unit and guide movement of the movable unit,
   wherein the encoder is disposed on a bottom side of the printed circuit board to face the movable unit.

4. The nucleic acid analysis system of claim 3, wherein the encoder comprises a magnetic or optical encoder.

5. The nucleic acid analysis system of claim 1, wherein each of the loaders comprises:
   a heating unit configured to control temperature of the cartridge on the loader; and
   a cartridge detecting sensor configured to detect whether a cartridge is on the loader.

6. The nucleic acid analysis system of claim 1, Wherein the fluorescence detecting module comprises:
   a first fluorescence detecting optical system configured to detect fluorescence using a first excitation light and a second excitation light of different wavelengths; and
   a second fluorescence detecting optical system configured to detect fluorescence using a third excitation light and a fourth excitation light of different wavelengths.

7. The nucleic acid analysis system of claim 6, wherein the first fluorescence detecting optical system comprises:
   a first objective lens configured to focus light on a reaction chamber of one of the plurality of cartridges;
   first and second light sources configured to emit the first excitation light and the second excitation light, respectively;
   a first dichroic mirror configured to reflect the first excitation light;
   a second dichroic mirror configured to reflect the second excitation light;
   a third dichroic mirror configured to reflect the first excitation light to the first objective lens and transmit the second excitation light to the first objective lens;
   a first photodetector configured to detect a first fluorescence emitted from a sample in the cartridge in response to the first excitation light; and
   a second photodetector configured to detect a second fluorescence emitted from the sample in the cartridge in response to the second excitation light.

8. The nucleic acid analysis system of claim 7, wherein the first fluorescence detecting optical system further comprises:
   a first collimating lens disposed proximal the first light source to collimate the first excitation light;
   a first excitation light filter configured to transmit only wavelengths of the first excitation light;
   a second collimating lens disposed proximal to the second light source to collimate the second excitation light; and
   a second excitation light filter configured to transmit only wavelengths of the second excitation light.

9. The nucleic acid analysis system of claim 7, wherein the first fluorescence detecting optical system further comprises:
   a first fluorescence filter configured to transmit only the first fluorescence;
   a first focusing lens disposed between the first fluorescence filter and the first photodetector to focus the first fluorescence on the first photodetector;
   a second fluorescence filter configured to transmit only the second fluorescence; and
   a second focusing lens disposed between the second fluorescence filter and the second photodetector to focus the second fluorescence on the second photodetector.

10. The nucleic acid analysis system of claim 7, wherein the first dichroic mirror is configured to reflect a wavelength band of the first excitation light and transmit a wavelength band of the first fluorescence,
    the second dichroic mirror is configured to reflect a wavelength band of the second excitation light and transmit a wavelength band of the second fluorescence, and
    the third dichroic mirror is configured to reflect wavelength bands of the first excitation light and the first fluorescence and transmit wavelength bands of the second excitation light and the second fluorescence.

11. The nucleic acid analysis system of claim 7, wherein the first light source and the second photodetector are disposed adjacent to each other on a first plane, and the second light source and the first photodetector are disposed adjacent to each other on a second plane substantially perpendicular to the first plane.

12. The nucleic acid analysis system of claim 6, wherein the second fluorescence detecting optical system comprises:
    a second objective lens configured to focus light on a reaction chamber of one of the plurality of cartridges;
    third and fourth light sources configured to emit the third excitation light and fourth excitation light, respectively;
    a fourth dichroic mirror configured to reflect the third excitation light;
    a fifth dichroic mirror configured to reflect the fourth excitation light;
    a sixth dichroic mirror configured to reflect the third excitation light to the second objective lens and transmit the fourth excitation light to the second objective lens;
    a third photodetector configured to detect a third fluorescence emitted from a sample in the cartridge in response to the third excitation light; and
    a fourth photodetector configured to detect a fourth fluorescence emitted from the sample in the cartridge in response to the fourth excitation light.

13. The nucleic acid analysis system of claim 12, wherein the fourth dichroic mirror is configured to reflect a wavelength band of the third excitation light and transmit a wavelength band of the third fluorescence,     the fifth dichroic mirror is configured to reflect a wavelength band of the fourth excitation light and transmit a wavelength band of the fourth fluorescence, and     the sixth dichroic mirror is configured to reflect wavelength bands of the third excitation light and the third fluorescence and transmit wavelength bands of the fourth excitation light and the fourth fluorescence.

14. The nucleic acid analysis system of claim 12, wherein the third light source and the fourth photodetector are disposed adjacent to each other on a third plane, and the fourth light source and the third photodetector are disposed adjacent to each other on a fourth plane substantially perpendicular to the third plane.

\* \* \* \* \*